(12) United States Patent
Hayman

(10) Patent No.: US 6,353,756 B2
(45) Date of Patent: *Mar. 5, 2002

(54) RADIOTHERAPY STENT

(76) Inventor: Michael Hayman, 9 Audubon Pl., New Orleans, LA (US) 70118

( * ) Notice: Subject to any disclaimer, the term of this patent is extended or adjusted under 35 U.S.C. 154(b) by 0 days.

This patent is subject to a terminal disclaimer.

(21) Appl. No.: 09/741,595

(22) Filed: Dec. 19, 2000

Related U.S. Application Data

(62) Division of application No. 09/295,621, filed on Apr. 20, 1999, now Pat. No. 6,192,271.

(51) Int. Cl.$^7$ .................................................. A61N 1/30
(52) U.S. Cl. ........................................................ 604/21
(58) Field of Search .................. 604/96, 21, 890.1, 604/891.1, 104–107; 606/198, 194, 191–193, 195; 623/1, 11, 12; 600/1–8

(56) References Cited

U.S. PATENT DOCUMENTS

| | | |
|---|---|---|
| 5,059,166 A | 10/1991 | Fischell et al. ............... 600/3 |
| 5,176,617 A | 1/1993 | Fischell et al. ............... 600/3 |
| 5,484,384 A | 1/1996 | Fearnot ........................ 600/3 |
| 5,498,227 A | 3/1996 | Mawad ........................ 600/3 |
| 5,643,464 A | 7/1997 | Rhee et al. ................. 210/748 |
| 5,662,580 A | 9/1997 | Bradshaw et al. ............. 600/3 |
| 5,756,553 A | 5/1998 | Iguchi et al. ............ 514/772.3 |
| 5,782,742 A | 7/1998 | Crocker et al. ............... 600/3 |
| 5,840,008 A | 11/1998 | Klein et al. ................... 600/3 |
| 5,891,108 A | 4/1999 | Leone et al. ................ 604/264 |
| 5,899,882 A | 5/1999 | Waksman et al. ............. 604/96 |
| 5,980,566 A | 11/1999 | Alt et al. .................... 604/198 |
| 6,019,779 A | 2/2000 | Thorud et al. .............. 606/198 |
| 6,039,757 A | 3/2000 | Edwards et al. ............ 606/194 |
| 6,192,271 B1 * | 2/2001 | Hayman ..................... 604/21 |

* cited by examiner

Primary Examiner—Manuel Mendez
(74) Attorney, Agent, or Firm—Keaty Professional Law Corporation

(57) ABSTRACT

A radiotherapy stent device has a flexible, collapsible mesh body that can be expanded in a blood vessel of a patient to deliver radiation to the tissue surrounding the site of stent implantation. One or more hollow sleeves are secured on the body. The sleeves are loaded with radioactive material immediately prior to positioning of the stent in the vascular structure. As a result, the shelf life of the stent is substantially increased, and dosage of the radiation can be more precisely controlled.

4 Claims, 3 Drawing Sheets

RADIOTHERAPY STENT

CROSS-REFERENCE TO RELATED APPLICATIONS

This application is a divisional application of my application Ser. No. 09/295,621 now U.S. Pat. No. 6,192,271 filed on Apr. 20, 1999, for "Radiotherapy Stent", the full disclosure of which is incorporated by reference herein.

BACKGROUND OF THE INVENTION

This invention relates to the field of radiotherapy, and more particularly to the field of intra-arterial stents that are used for implanting at or adjacent the side of treatment of cancer cells or other patholitical conditions in a human body.

The intra-arterial stents have been widely used to prevent restenosis following angioplasty, wherein a coronary artery is dilated with a balloon. In time, the artery widened by an implanted balloon tends to close due to elastic recoil of the tissue. In the past, one of the solutions was to use a stent with radiation material embodied into the body of the implant in order to maintain patency of the artery following angioplasty. However, implantation of the stent often leads to intimal hyperplasia in about six months and causes closure of the artery again.

One example of a stent which utilizes a radioisotope imbedded into an arterial stent has been disclosed in U.S. Pat. No. 5,059,166 issued on Oct. 22, 1991 to Fischell et al. In that patent, the stent is implanted at a place in the artery wherein it irradiates a tissue in close proximity to the implantation site of the stent and reduces the tissue growth following a balloon angioplasty. The stent according to '166 patent has a cross section of two turns of a coil spring fabricated from a pure metal or alloy, which has been irradiated to become radioactive. The radioisotope used in '166 patent may be an alpha-beta or gamma emitter. The half life is between 10 hours and 100 days. The most preferable embodiment would have a half life of 16 days.

One of the disadvantages of this type of stent is that it presents a considerable storage problem. The half life of the isotope is very limited, and a surgeon or radiation oncologist has to keep a continuously fresh supply of stents ready for his use during an implantation surgery. Once the isotope has lost its effectiveness, the stent has to be discarded and new stents have to be purchased. Therefore, the physician is required to predict how many stents he would require during a particular period of time and order only the required amount, so as to not waste the valuable devices.

Another example of a radioactive stent is disclosed in U.S. Pat. No. 5,213,561 issued on May 25, 1993. In that patent, the radioactive source is mounted at the distal end of a guide wire, or in a balloon catheter. A balloon expansible stent as is inserted through the vascular structure to the site of radiation treatment. The flexible member is inserted longitudinally through the structure and a radioactive source mounted at the distal end of the flexible member becomes placed at the end of the tube, inside the balloon. An outer sleeve of the guide wire slides over the inner wire for a distance sufficient to cover and uncover radioactive material, so that the shield formed by the outer sleeve can be moved away from the radioactive material and expose the angioplasty site to radiation. After the exposure, the outer sleeve is shifted again to cover the radioactive section. The device is designed to selectively prevent exposure of the walls of the vascular structure when the guide wires are inserted or being removed.

Still another example of a radioactive stent is disclosed in U.S. Pat. No. 5,572,984 issued on Mar. 3, 1998 to Fischell et al. There, a radioactive coating on an embedded radioactive isotope performs both antithrombogenic and radioactive function. The preferred embodiment of '984 patent discloses a phosphorylcholine coated stent where some of the phosphate groups contain phosphorus 32. Another example of a stent prepared with a radioactive coating is disclosed in U.S. Pat. No. 5,176,617 issued on Jan. 5, 1993 to Fischell et al. In that patent, the stent is a tubular, thin-walled structure that extends radially outward against the wall of the vessel, with a part of the stent being formed from a radioisotope material.

In all these patents, the radioisotope is integral to a stent and is designed to irradiate tissue in close proximity to the implantation site of the stent. Some of the devices are designed to reduce malignant cell growth in a blood vessel, for example a bile duct, while others are designed to maintain vessel patency without injuring the surrounding tissue. All of the above patents suffer from the same disadvantage; they have a limited shelf life, and a supply of them must be continuously replaced in order to provide more benefits to the patient.

The present invention contemplates elimination of drawbacks associated with the prior art and provision of a radiotherapy stent that has a more or less unlimited shelf life and can be loaded with radioactive material immediately prior to positioning in a human body.

SUMMARY OF THE INVENTION

It is, therefore, an object of the present invention to provide a radiotherapy stent suitable for implanting into a blood vessel for delivering radioactive rays to the tissue surrounding the implantation site.

It is another object of the present invention to provide a stent capable of inhibiting intimal hyperplasia of a blood vessel following balloon angioplasty.

It is a further object of the present invention to provide a radiation stent assembly with unlimited shelf life, capable of being assembled immediately prior to implantation.

These and other objects of the present invention are achieved through a provision of a device and method for delivering radioactive energy to a patient=s vascular system. The device of the present invention comprises a stent assembly having a mesh body, at least one hollow sleeve secured to an exterior wall of the mesh body and radioactive member that is loaded into the sleeve immediately prior to inserting of the stent assembly into the blood vessel. The stent assembly can be made with a plurality of sleeves, allowing more radioactive material to be delivered to the treatment site. The mesh body can be delivered to the treatment site by any suitable means, such as a balloon device, a catheter and the like. Once the collapsed stent assembly is delivered to the desired position in the vessel, it is expanded such that the elongated sleeve aligns itself along the wall of the blood vessel, while the assembly lodges against the inner wall of the blood vessel.

The radioactive material contained in the sleeve emits radioactive rays, preventing restenosis of the blood vessel following angioplasty. The same stent device and method can be used for radiotherapy of the patient, where the dose of radiation can be controlled by the amount and strength of the radioactive material loaded into the sleeve.

The radioactive material can be made in the form of small pellets, or balls, or in the form of tiny cylinders that are secured together end-to-end to form a continues string, or line. The open ends of the sleeve are closed in any desired manner to prevent the radioactive material from escaping the sleeve during and after positioning of the device in the vascular system of a patient.

BRIEF DESCRIPTION OF THE DRAWINGS

Reference will now be made to the drawings, wherein like parts are designated by like numerals, and wherein.

DETAIL DESCRIPTION OF THE PREFERRED EMBODIMENT

Figures 1, 2:
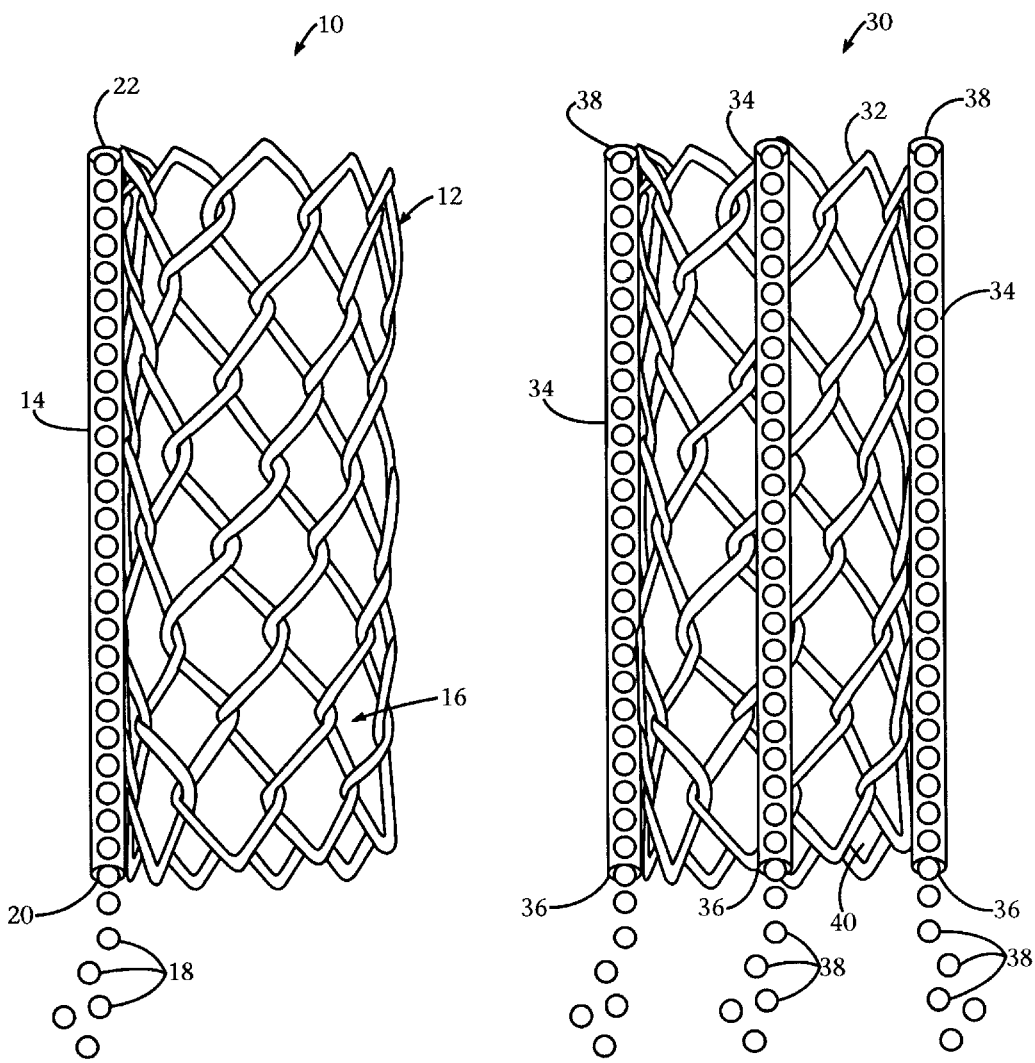
FIG. 1 is a detail view of the first embodiment of the device according to the present invention utilizing one channel for receipt of radioactive pellets.
FIG. 2 is a detail view of a second embodiment of the present invention, wherein multiple channels are provided and incorporated in the stent assembly for receiving pelletized radioactive members.

Turning now to the drawings in more detail, numeral 10 designates a stent assembly in accordance with the first embodiment of the present invention. As can be seen in the drawing, the stent assembly 10 comprises a stent body 12 and one sleeve 14 fixedly attached to the wall of the stent body 12. The sleeve 14 extends longitudinally along the exterior wall of the mesh body 12, in a parallel relationship to a longitudinal axis along the body 12.

Both body 12 and the sleeve 14 are made from a flexible, resilient material, such as metal wire or plastic. The body 12, when collapsed, that can assume any randomly selected shape. When the body 12 capable is expanded it forms a tubular body shown in FIG. 1 that defines an annular space 16 therein. The wall of the body 12 is formed as a lattice of intermeshed wire or string, so as to allow easy liquid circulation through the annular space 16 and through the openings formed in the lattice work.

The stent assembly 10, when positioned in a blood vessel (not shown), may be positioned intraluminally by means of a catheter inserted into the blood vessel, similar to an angioplasty catheter, or by other suitable means well known to those skilled in the art. The stent body 12 can be expanded by a balloon that is mounted at the distal end of the catheter to slightly fit against the walls of the blood vessel and lodge the stent at the desired site.

Prior to inserting of the stent assembly 10 into the artery, the stent is loaded with radioactive members 18 which can be formed in any desired shape or form. As shown in FIG. 1, the radioactive member 18 can be formed with a plurality of tiny pellets having radioactive properties. The sleeve 14, being a hollow cylindrical sleeve, has at least one open end 20 through which the pellets, or balls 18 are loaded.

Prior to loading, the radioactive pellets 18 are stored separately from the stent assembly 10 and are inserted into the opening 20 to fill the sleeve 14 to the desired volume. A surgeon, knowing the radioactive capability of the pelletized radiation medium can select the desired quantity of the pellets 18 to be delivered to the radiation site. Following loading of the pellets 18 into the sleeve 14, the opening 20 is closed, so as to prevent escape of the radioactive material from the assembly 10.

The opposite end 22 of the sleeve 14 may be either open during loading of the pellets 18 or sealed during manufacture, leaving only end 20 for positioning of the pellets in the sleeve 14. Of course, if desired, the opposite end of the sleeve can be used contemporaneously with the end for loading of the pellets, or along, with the end 20 normally closed.

Turning now to the embodiment in FIG. 2, the radiotherapy stent is shown to comprise a body 32 made in the form of lattice-like mesh that carries a plurality of sleeves 34 on the exterior surface thereof. The sleeves 34 are fixedly attached to the body 32 to expand in a longitudinal direction along the length of the body 32. Each sleeve 34, similarly to the sleeve 14, has at least one open end, through which pelletized radioactive material 38 is inserted. The opposite ends 38 of the sleeves 34 can be sealed at the fabrication site or plugged prior to inserting the pellets 38 into the sleeves 34.

Figure 5:
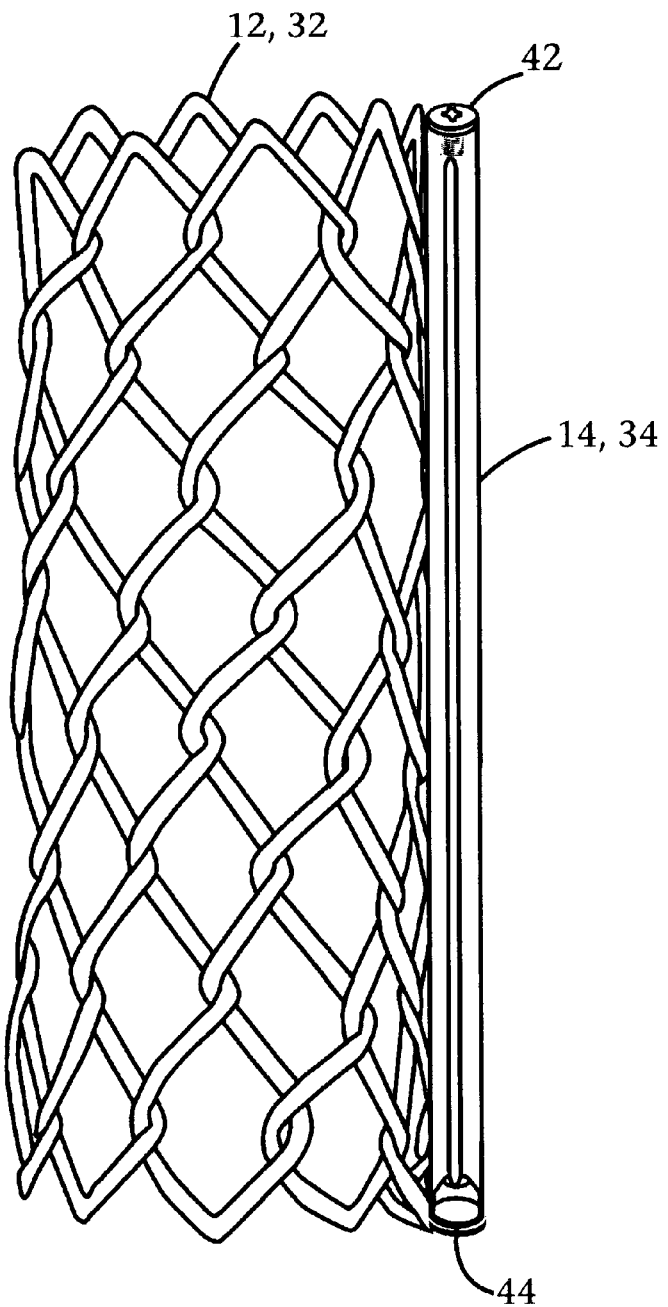
FIG. 5 is a detailed view of a stent assembly, where the tube is closed at both ends to prevent the radioactive material from escaping the tube.

Similarly to the body 12, the body 32 offers minimal resistance to the blood flow passing through the annular space 40 defined by the body 32. Similarly to the embodiment of FIG. 1, the sleeve 34 can be sealed at the end 36 after the pelletized radioactive material 38 is inserted therein. As shown in FIG. 5, the ends of the sleeve 14, 34 can be sealed by a first plug 42 at one end and by a plug 44 at the opposite end. Of course, other suitable means of closing the open ends of the sleeve can be provided, depending on the manufacturing technology employed.

Figure 3:
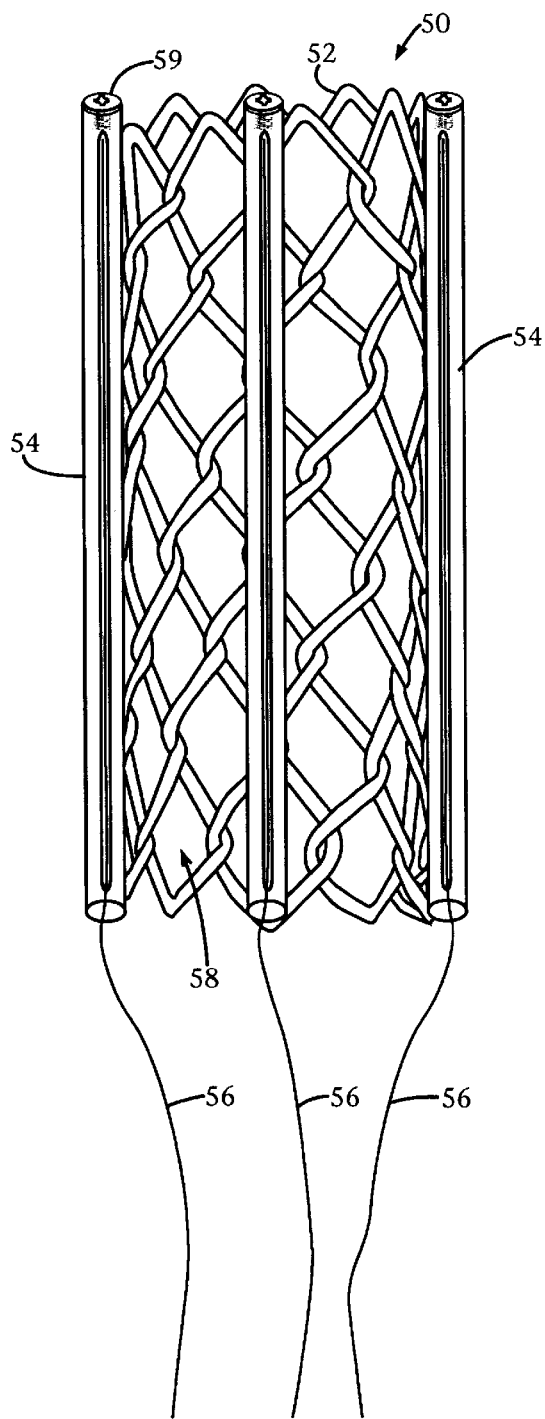
FIG. 3 is a detail view of the third embodiment of the present invention utilizing multiple channels for receipt of a string-like radioactive material.

Turning now to FIG. 3, the third embodiment of the stent device of the present invention is shown to comprise a radiotherapy stent assembly 50 comprising a stent body 52 and a plurality of sleeves 54. The stent body 52, similarly to the stent bodies 12 and 32, is formed as lattice-type mesh body from metal, metal alloy or plastic wire or string. Each sleeve 54 is adapted to receive radioactive material therein.

The radioactive member in this embodiment is formed as a continuous string 56, which can be manufactured in the form of tiny cylindrical bodies secured together end-to-end to form a continuous line. Alternatively, the radioactive member 56 may be formed as a radioactive wire with a core and a radioactive coating thereon, or by other suitable means available at the manufacturing facility.

Prior to inserting the stent 50 into the blood vessel of the patient, the strings 56 are kept in a separate container, wherein their shelf life can be prolonged to a desired period of time. Immediately prior to inserting the stent 50 into the patient's body, the strings 56 are positioned in their respective sleeves 54 to approximately correspond to the length of the sleeve 54. As with the embodiments of FIGS. 1 and 2, the stent body 52 forms an annular channel 58 within the extended latticework to allow free circulation of blood through the artery.

Figure 4:
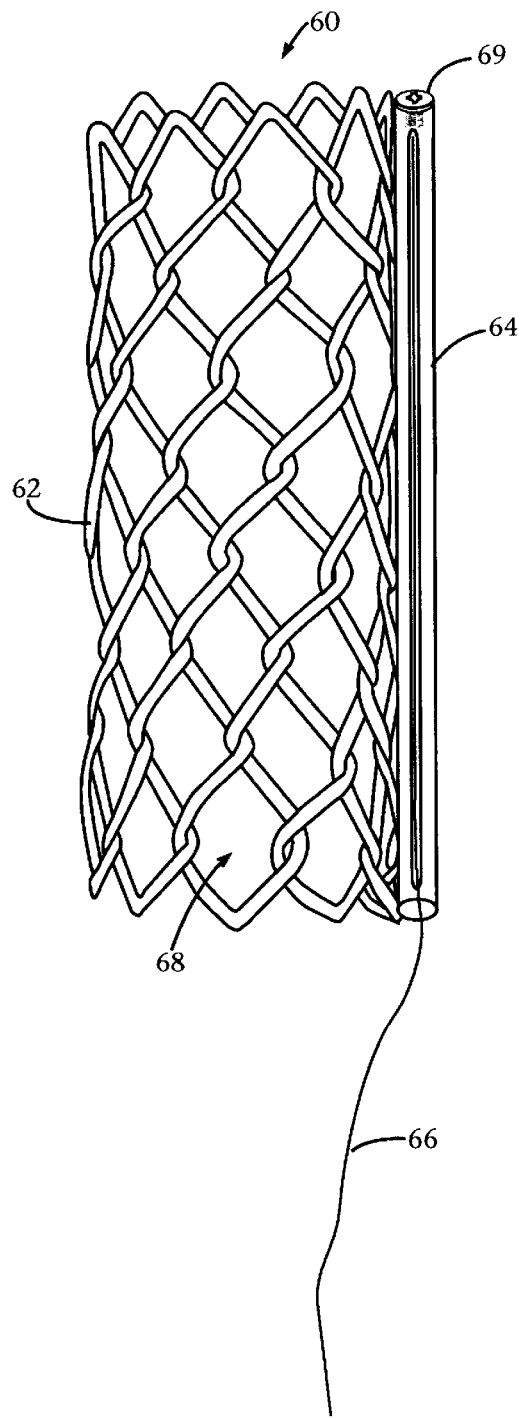
FIG. 4 is a detailed view illustrating a fourth embodiment of the present invention with one channel for receipt of string-like radioactive material.

The embodiment of FIG. 4 is similar to the embodiment of FIG. 3 inasmuch as it uses a continuous string of radioactive material. The stent assembly 60 shown in FIG. 4 is comprised of a stent body 62 and one sleeve 64 adapted to receive the continuous string of radioactive material 66. Upper one of the open ends of the sleeves 54 and 64 can be pre-sealed during manufacturing, or closed with plugs 59 and 69, respectively.

The body 62 is shown as a latticework mesh, which, when expanded, defines an annular space 68 therein. The continuous line 66, similar to the line 56, can be formed in any desired manner and sized to correspond to the longitudinal dimensions of the sleeve 64.

The radioactive material utilized in the present invention is designed to deliver the intended dosage of radiation to the stenosis, where the fibrous tissue has grown following an angioplasty procedure. Additionally, the stent device of the present invention may be used for positioning at a site of malignant growth to deliver radiation at a rate necessary for radiotherapy treatment of the patient. The radioactive material may be selected from any desired material available for medical uses. For example, cobalt-60, casium-137, palladium-103, and a number of others can successfully be used with the stent assembly of the present assembly.

The radiation dose will be pre-determined at the time the radioactive material in the form of pellets, continuous lines, etc. is manufactured. Similarly, the radiation dose will be adjusted depending on the intended use of the stent assembly, whether it is to be used for radiation therapy or for combating fibrointimal proliferation.

In operation, the stent assembly of the present invention may be delivered to the site by a balloon device according to a procedure well familiar to medical practitioners. The balloon device carries the stent assembly of the present invention and delivers it to the site of treatment. When the balloon is inflated, the stent body is expanded, as well, such that the mesh of the stent body forms a cylindrical channel in the vascular system of the patient. When the balloon is deflated, the stent assembly remains lodged in place, delivering the intended radiation and maintaining the patency of the partially occluded vessel.

In the alternative, the stent assembly may be delivered by attaching it to a metal wire and inserting it into the artery or duct of the patient. The delivery catheter, after it has successfully positioned the stent assembly in the patient body, is withdrawn, leaving the stent assembly in place.

One of the main advantages of the present invention is extension of the shelf life of the radioactive stent. The stent assemblies are shipped to the physician separate from the radioactive members, allowing the physician to load the radiation material immediately prior to implantation of the stent in the patient body. An additional advantage, of course, allows the physician to select the radioactive material depending on the intended purpose of the stent and also to select the dosage of the radioactive material delivered to the site of treatment. The half-life of the radioactive material can be anywhere between several hours to 1000 days.

Many changes and modifications can be made in the design of the present invention without departing from the spirit thereof. I therefore pray that my rights to the present invention be limited only by the scope of the appended claims.

I claim:

1. An intra-arterial stent device, comprising:

a stent assembly comprised of a stent body adapted to engage a wall of a blood vessel, said stent body being transparent to fluid flow and at least one hollow non-fenestrated sleeve attached to an exterior wall of the stent body, said at least one sleeve extending along substantially entire length of the stent body in parallel relationship to a longitudinal axis of the stent body after the stent assembly has been positioned in the blood vessel; and a source of radioactive members adapted for loading into said at least one sleeve immediately prior to inserting said stent assembly into the blood vessel and wherein each of said radioactive members comprises an elongated string containing radioactive material having a pre-determined value of emitted radioactive energy.

2. The device of claim 1, wherein said radioactive material is a radioisotope.

3. The device of claim 1, wherein said radioactive material is capable of decreasing restenosis of the blood vessel following an angioplasty procedure.

4. The device of claim 1, wherein said radioactive material is capable of decreasing growth of malignant cells in a body tissue surrounding said blood vessel.

* * * * *